(12) United States Patent
Morris et al.

(10) Patent No.: US 10,722,280 B2
(45) Date of Patent: Jul. 28, 2020

(54) IMPLANT OF OSTEOSTIMULATIVE MATERIAL

(71) Applicant: Bone Solutions, Inc., Colleyville, TX (US)

(72) Inventors: Frankie L. Morris, Colleyville, TX (US); Drew Diaz, Colleyville, TX (US)

(73) Assignee: Bone Solutions, Inc., Colleyville, TX (US)

( * ) Notice: Subject to any disclaimer, the term of this patent is extended or adjusted under 35 U.S.C. 154(b) by 195 days.

(21) Appl. No.: 15/939,981

(22) Filed: Mar. 29, 2018

(65) Prior Publication Data
US 2018/0280589 A1  Oct. 4, 2018

Related U.S. Application Data

(60) Provisional application No. 62/478,241, filed on Mar. 29, 2017.

(51) Int. Cl.
*A61F 2/44* (2006.01)
*A61B 17/86* (2006.01)

(52) U.S. Cl.
CPC .......... *A61B 17/866* (2013.01); *A61B 17/864* (2013.01); *A61B 17/8625* (2013.01); *A61F 2/447* (2013.01)

(58) Field of Classification Search
CPC . A61B 17/86; A61B 17/8605; A61B 17/8625; A61B 17/864; A61B 17/8645; A61B 17/866; A61F 2/44; A61F 2/4455; A61F 2/447
See application file for complete search history.

(56) References Cited

U.S. PATENT DOCUMENTS

| | | | | |
|---|---|---|---|---|
| 4,871,384 A * | 10/1989 | Kasuga | ............ | A61L 27/12 65/30.1 |
| 6,383,519 B1 * | 5/2002 | Sapieszko | ........... | C04B 38/0025 424/401 |
| 6,458,162 B1 * | 10/2002 | Koblish | ............... | A61B 17/866 423/305 |
| 2004/0267263 A1 * | 12/2004 | May | ..................... | A61B 17/842 604/502 |
| 2007/0032877 A1 * | 2/2007 | Whiteside | ........... | A61F 2/30767 623/22.15 |
| 2010/0023030 A1 * | 1/2010 | Remia | ................ | A61B 17/8685 606/151 |
| 2011/0283919 A1 * | 11/2011 | Price | .................... | A61B 17/866 106/160.1 |
| 2012/0156477 A1 * | 6/2012 | Kurze | ................... | A61L 27/047 428/336 |
| 2013/0304134 A1 * | 11/2013 | Tamai | .................. | A61L 27/047 606/301 |
| 2016/0015523 A1 * | 1/2016 | Lewis | ............... | A61B 17/1631 623/17.16 |
| 2017/0086897 A1 * | 3/2017 | Honda | ................... | A61B 17/68 |
| 2017/0246356 A1 * | 8/2017 | Preiss-Bloom | ....... | A61F 2/4455 |
| 2018/0280589 A1 * | 10/2018 | Morris | .................... | A61L 31/16 |

(Continued)

*Primary Examiner* — Eric S Gibson
(74) *Attorney, Agent, or Firm* — McDonnell Boehnen Hulbert & Berghoff LLP

(57) ABSTRACT

The present disclosure provides a bone-implantable device and methods of use. The bone-implantable device comprises a body having an exterior surface, wherein a portion of the exterior surface includes a cured osteostimulative material comprising MgO.

17 Claims, 4 Drawing Sheets

(56) References Cited

U.S. PATENT DOCUMENTS

2018/0344894 A1* 12/2018 Kay ................... A61B 90/39
2019/0125420 A1*  5/2019 Diaz .................. A61B 17/866
2019/0282736 A1*  9/2019 Preiss-Bloom ....... A61L 31/148

* cited by examiner

IMPLANT OF OSTEOSTIMULATIVE MATERIAL

RELATED APPLICATIONS

This application claims priority to U.S. Provisional Application No. 62/478,241 entitled "Implant of Osteostimulative Material," filed on Mar. 29, 2017, the contents of which are hereby incorporated by reference in its entirety.

FIELD OF THE INVENTION

The invention relates to the field of bone implantable devices integrated with osteostimulative material.

BACKGROUND OF THE INVENTION

Unless otherwise indicated herein, the materials described in this section are not prior art to the claims in this application and are not admitted to be prior art by inclusion in this section.

Implant loosening is commonly encountered in humans and other animals that undergo orthopedic surgery and results in compromised construct stability, decreased patient comfort, and additional expenses. The holding power of an implant in bone is associated with multiple factors such as the mechanical and structural properties of the implant, mechanical and physical properties of the bone, placement of the implant, load distribution, and bone-implant integration. Cyclic loading, infection, inflammatory reaction around the implant and subsequent bone resorption, micromotion-induced implant loosening, and fatigue failure at the bone-implant or bone-cement interface are other common causes of implant failure.

Various implant surface configurations, coating methods, and biomaterials have been developed to improve integration between bones and implants. An assortment of osteoinductive and osteoconductive materials has been used to fill bone defects and to anchor implants to bone. To achieve this, a material should adhere implant to bone, tolerate and transfer loads on the implant to bone, promote bone healing, and be readily absorbed at a rate that allows adequate time for osseointegration.

The biomechanical properties of the filler material should resemble those of bone and should be resistant to fragmentation and wear debris formation. Furthermore, the formulation should be easy to apply, should not cause thermal damage during the process of curing, and should be tolerated by the host.

Polymethylmethacrylate is an acrylic bone cement, which has been used for plate luting and total arthroplasties for almost 50 years. Because PMMA is nonabsorbable, two interfaces will inevitably exist: one between the implant and cement and another between the cement and bone. Wear particle formation, thermal necrosis from the curing process, and fractures within the cement layer are known complications associated with the use of PMMA and can lead to failure of the implant construct. Calcium-phosphate cement was the first biodegradable bone cement to be made commercially available. It can tolerate high compressive strength, fill in gaps between implant and bone, act as an osteoconductive medium, and increase biomechanical strength of the bone-implant interface. However, calcium phosphate cement lacks adhesive properties and has a long absorption time.

In addition, existing osteostimulative materials must disadvantageously be applied immediately before implantation. Such a requirement increases the procedure time, and increases the risk of uneven application of the osteostimulative material on an implant.

SUMMARY OF THE INVENTION

In view of the foregoing, the inventors recognized that a bone-implantable device with an improved osteostimulative material integrated at the point of sale would be desirable. The present invention provides such a device and method of use.

Thus, in a first aspect, the present invention provides a bone-implantable device comprising a body having an exterior surface, wherein a portion of the exterior surface includes a cured osteostimulative material comprising MgO.

In a second aspect, the present invention provides a method for securing a bone portion using a bone-implantable device, the method comprising: (a) providing the bone-implantable device, the bone-implantable device comprising a body having an exterior surface with a portion of the exterior surface comprising a cured, MgO-containing osteostimulative material, and (b) securing the bone-implantable device to the bone portion so that said cured osteostimulative material contacts the bone portion.

These as well as other aspects, advantages, and alternatives, will become apparent to those of ordinary skill in the art by reading the following detailed description, with reference where appropriate to the accompanying drawings.

DETAILED DESCRIPTION

Figure 1:
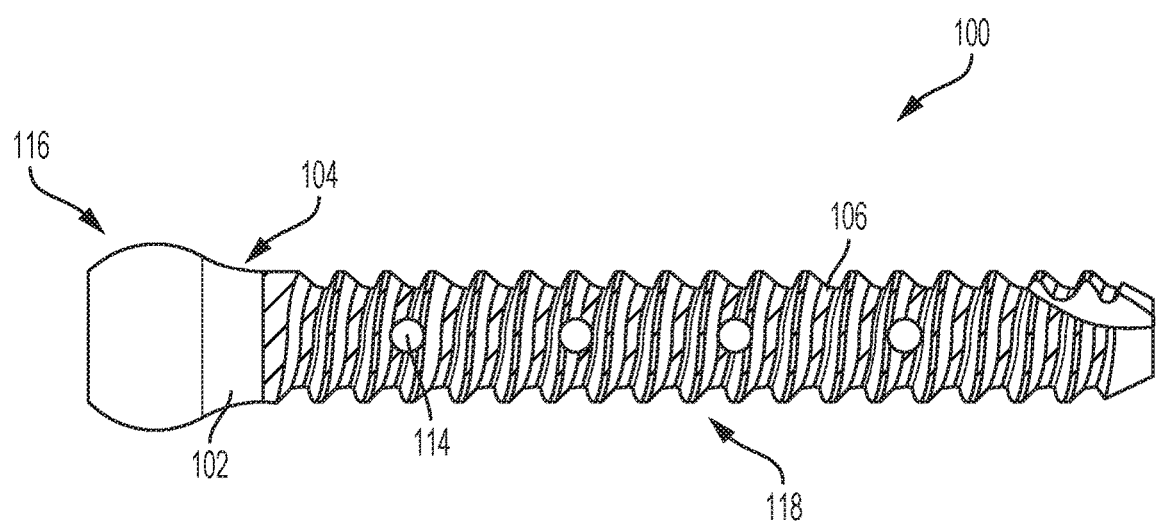
FIG. 1 illustrates a side view of a bone screw according to an exemplary embodiment of the invention.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The exemplary embodiments described herein are not meant to be limiting. It will be readily understood that the aspects of the present disclosure, as generally described herein and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, "osteostimulative" refers to the ability of a material to improve healing of bone injuries or defects.

As used herein, "osteoconductive" refers to the ability of a material to serve as a scaffold for viable bone growth and healing.

As used herein, "osteoinductive" refers to the capacity of a material to stimulate or induce bone growth.

As used herein, "biocompatible" refers to a material that elicits no significant undesirable response when inserted into a recipient (e.g., a mammalian, including human, recipient).

As used herein, "bioresorbable" refers to a material's ability to be resorbed in-vivo through bodily processes. The resorbed material may be used by the recipient's body or may be excreted.

As used herein, "cured" refers to a material that has transformed from a slurry to a solid, by providing adequate moisture, temperature, and/or time or by other means.

With reference to the Figures, FIGS. 1-8 illustrate exemplary bone-implantable devices 100. The bone-implantable device 100 may include a body 102 having an exterior surface 104. A portion of the exterior surface 104 includes a cured osteostimulative material 106 comprising Magnesium oxide (MgO). The body 102 of the bone-implantable device 100 may comprise titanium, polyetheretherketone (PEEK), polyurethane, bone, or combinations thereof. The cured osteostimulative material 106 may have both osteoconductive and osteoinductive properties. In addition, the cured osteostimulative material 106 may be bioresorbable. A thickness of the cured osteostimulative material 106 on the exterior surface 104 of the body 102 may range from about 20 µm to about 200 µm. In some examples, the cured osteostimulative material 106 does not cover the entirety of the exterior surface 104 of the bone-implantable device such that there are areas of bare titanium polyetheretherketone (PEEK), polyurethane, and/or bone.

Figure 2:
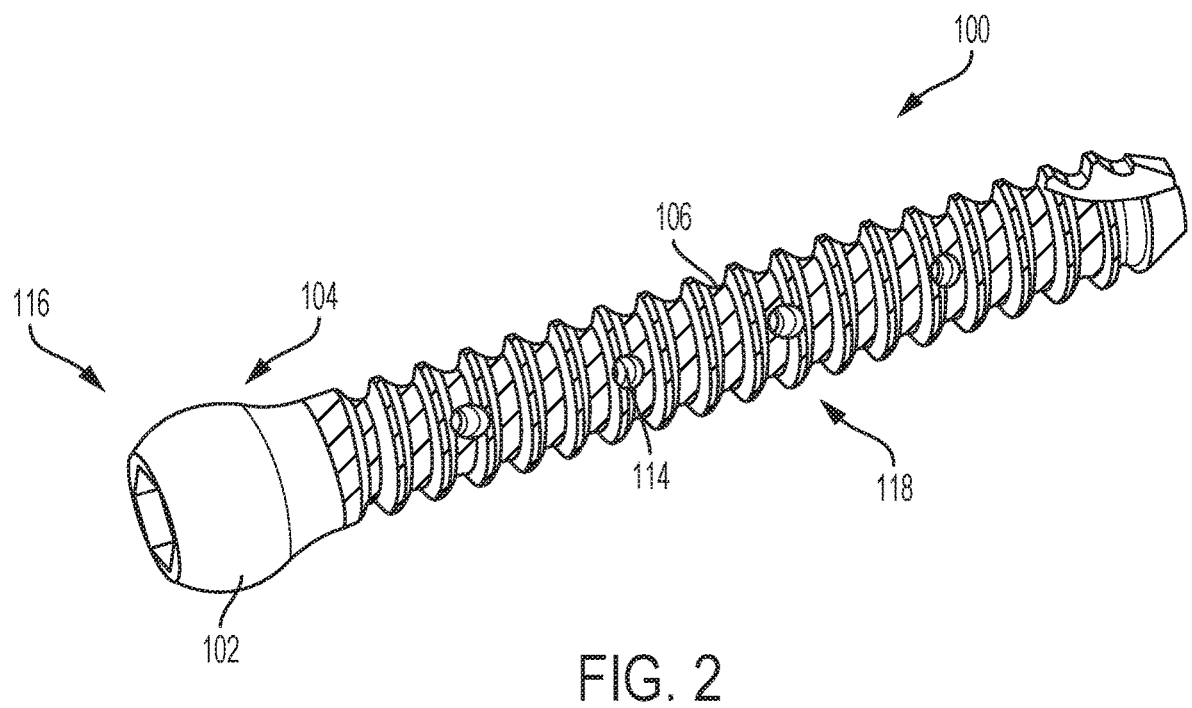
FIG. 2 illustrates a perspective view of the bone screw of FIG. 1 according to an exemplary embodiment of the invention.

In one example, as shown in FIGS. 1-2, the bone-implantable device 100 comprises a bone screw including a head portion 116 and a threaded portion 118. In such an example, at least a portion of the threaded portion 118 includes the cured osteostimulative material 106. In one example, the cured osteostimulative material 106 is positioned in the valleys defined by the threads of the threaded portion 118. The area between threads of the threaded portion 118 may be rough, which may help to secure the osteostimulative material 106 to the threaded portion 118. In another example, the cured osteostimulative material 106 is positioned on the peaks between one or more of the threads of the threaded portion 118. In yet another example, the cured osteostimulative material 106 is positioned both in the valleys defined by the threads of the threaded portion 118 and on the peaks between one or more of the threads of the threaded portion 118. In such an example, the cured osteostimulative material 106 may not cover the entirety of the exterior surface 104 of the bone-implantable device such that there are areas of bare titanium polyetheretherketone (PEEK), polyurethane, and/or bone between the cured osteostimulative material 106 positioned in the valleys defined by the threads of the threaded portion 118 and the cured osteostimulative material 106 positioned on the peaks between one or more of the threads of the threaded portion 118. Such an arrangement is illustrated in FIGS. 1-2.

Figure 3:
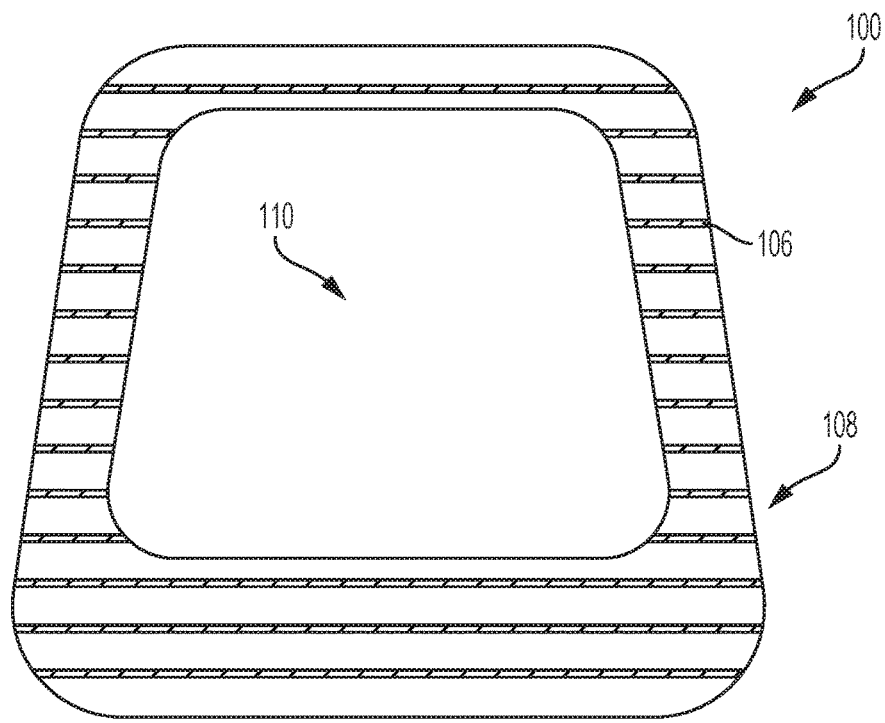
FIG. 3 illustrates a top view of an inter-vertebrate implant according to an exemplary embodiment of the invention.
Figure 4:
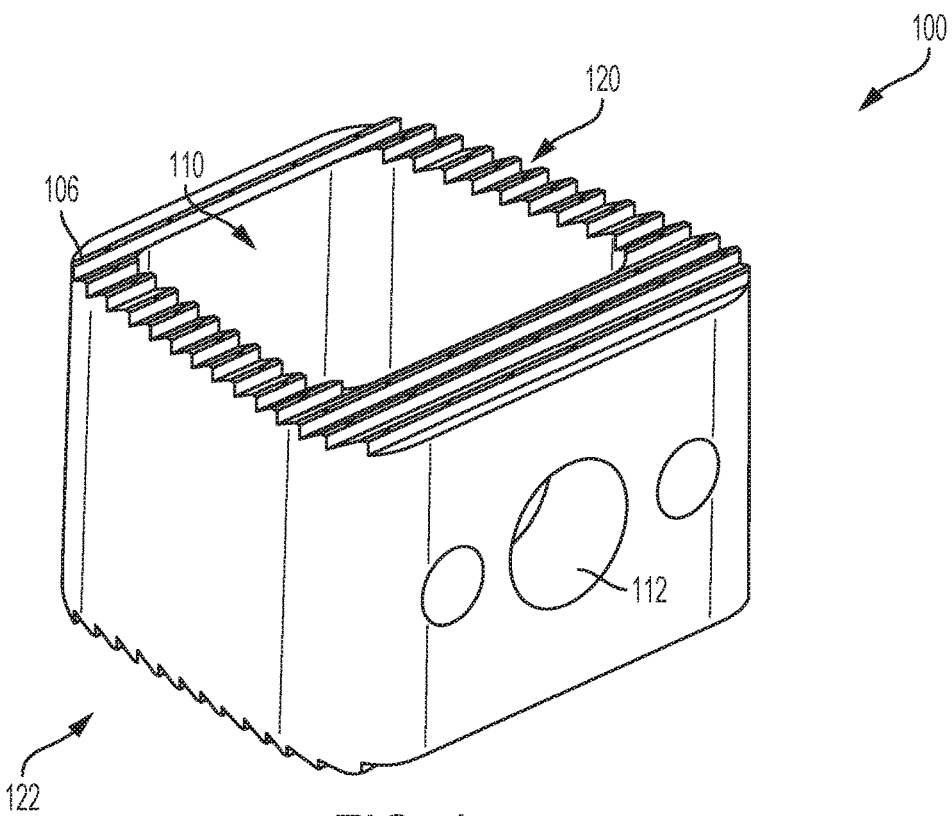
FIG. 4 illustrates a perspective view of the inter-vertebrate implant of FIG. 3 according to an exemplary embodiment of the invention.
Figure 5:
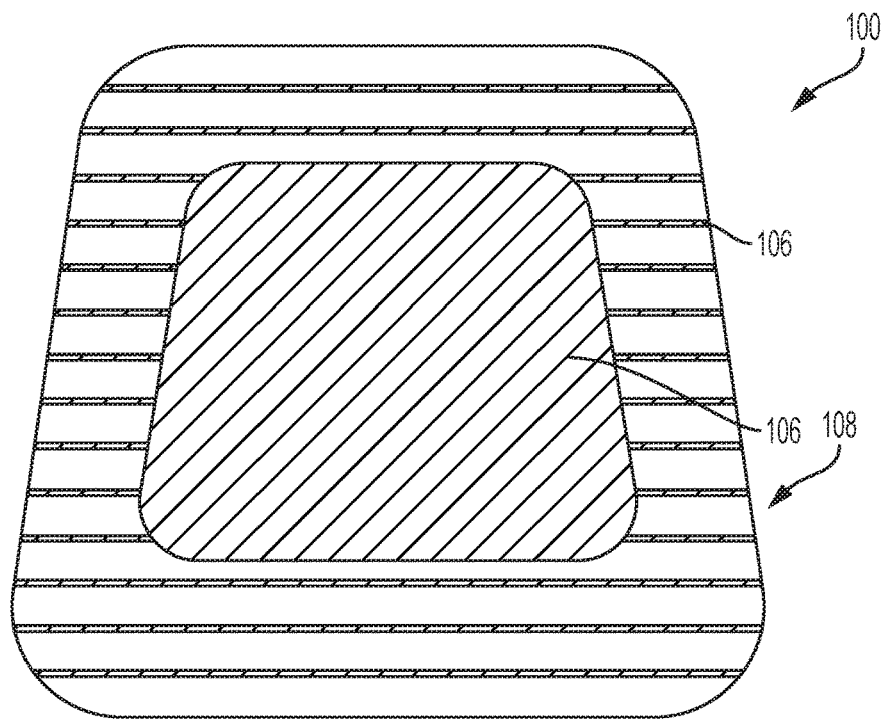
FIG. 5 illustrates a top view of an inter-vertebrate implant with osteostimulative material positioned in an interior cavity according to an exemplary embodiment of the invention.
Figure 6:
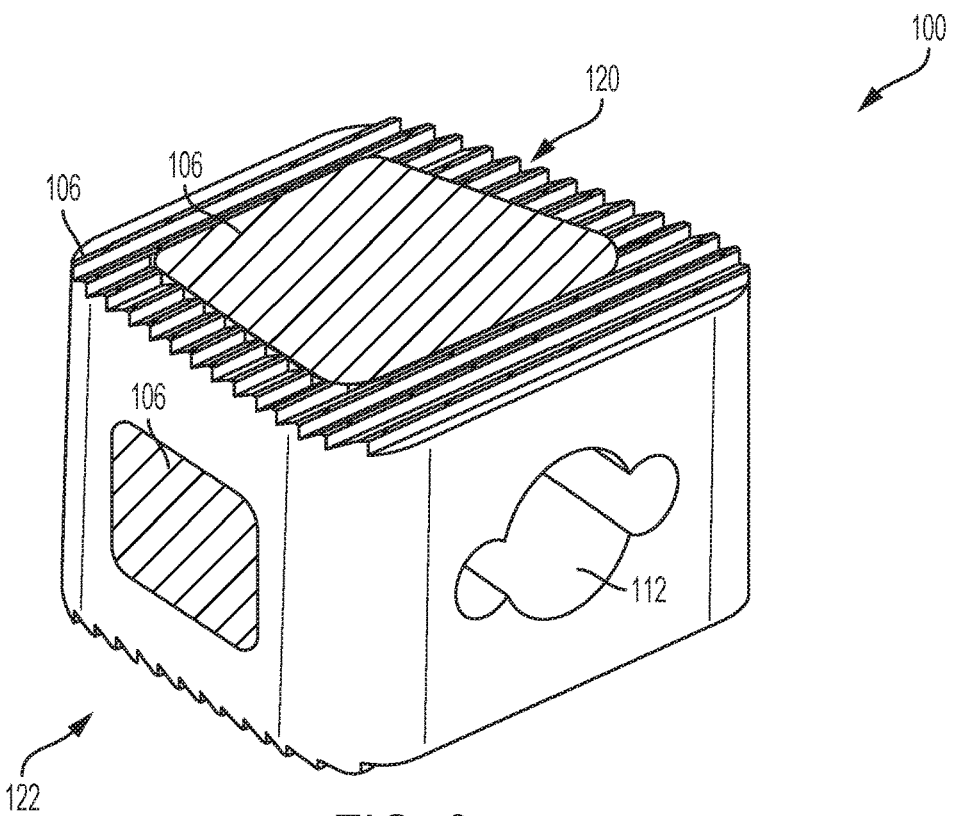
FIG. 6 illustrates a perspective view of the inter-vertebrate implant of FIG. 5 according to an exemplary embodiment of the invention.

In another example, the body 102 includes an interior cavity 110 and one or more openings 112 connecting the interior cavity 110 to the exterior surface 104, such as illustrated in FIGS. 3-4. In such an example, at least a portion of the interior cavity 110 and at least a portion of the one or more openings 112 includes the cured osteostimulative material 106. In yet another example, the exterior surface 104 includes a plurality of pores 114, and the cured osteostimulative material 106 is positioned in one or more of the plurality of pores 114, such as illustrated in FIGS. 1-2.

In another example, as shown in FIGS. 3-6, the exterior surface 104 of the bone-implantable device 100 includes a plurality of grooves 108, and the cured osteostimulative material 106 is positioned in one or more of the plurality of grooves 108. In particular, as shown in FIGS. 3-6, the bone-implantable device 100 may comprise an inter-vertebrate implant having a top grooved surface 120 and a bottom grooved surface 122. In such an example, at least a portion of each of the top grooved surface 120 and the bottom grooved surface 122 includes the cured osteostimulative material 106. In one example, the cured osteostimulative material 106 is positioned in one or more of the plurality of grooves 108 of the top grooved surface 120 and the bottom grooved surface 122. The plurality of grooves 108 on each of the top grooved surface 120 and the bottom grooved surface 122 may be rough, which may help to secure the osteostimulative material 106 to the exterior surface 104 of the bone-implantable device 100. In another example, the cured osteostimulative material 106 is positioned on the peaks between one or more of the plurality of grooves 108 of each of the top grooved surface 120 and the bottom grooved surface 122. In such an example, the cured osteostimulative material 106 is not positioned in the plurality of grooves 108 themselves, but instead is positioned on the peaks between the plurality of grooves 108.

Figure 7:
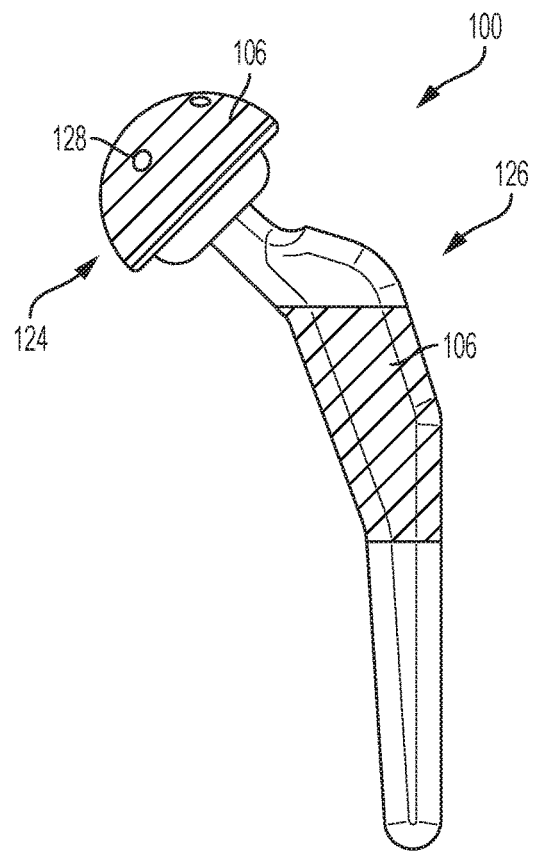
FIG. 7 illustrates a side view of a joint implant according to an exemplary embodiment of the invention.
Figure 8:
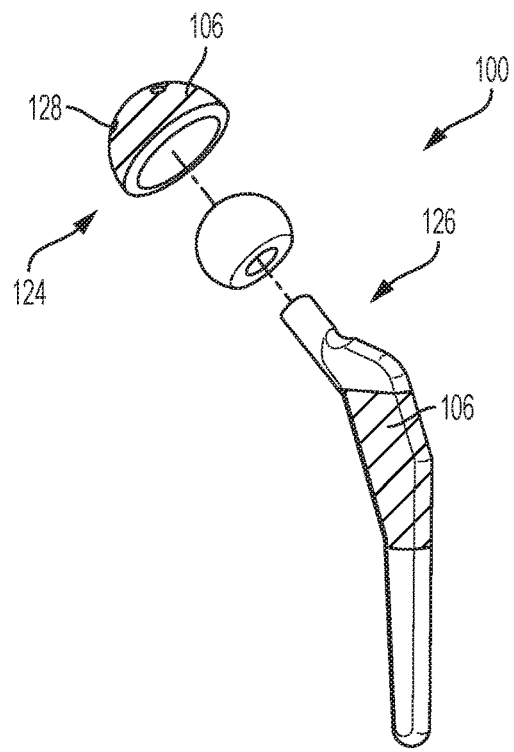
FIG. 8 illustrates an exploded view of the joint implant of FIG. 7 according to an exemplary embodiment of the invention.

In yet another example, as shown in FIGS. 7-8, the bone-implantable device 100 comprises a joint implant including a stationary component 124 coupled to a rotatable elongated member 126. In such an example, at least a portion of an exterior surface 104 of the stationary component 124 and at least a portion of the rotatable elongated member 126 includes the cured osteostimulative material 106.

In accordance with a further aspect of the invention, the bone-implantable device 100 may additionally carry one or more therapeutic agents for achieving further enhanced bone fusion and ingrowth. In one particular example, the bone-implantable device 100 may include one or more cavities 128 containing a therapeutic agent in the exterior surface 104 of the body 102. Such therapeutic agents may include natural or synthetic therapeutic agents such as bone morphogenic proteins (BMPs), growth factors, bone marrow aspirate, stem cells, progenitor cells, antibiotics, or other osteoconductive, osteoinductive, osteogenic, bio-active, or any other fusion enhancing material or beneficial therapeutic agent.

The resultant bone-implantable device 100 exhibits relatively high mechanical strength for load bearing support, while additionally and desirably providing high osteoconductive and osteoinductive properties to achieve enhanced bone ingrowth and fusion. In use, the cured osteostimulative material 106 positioned on the exterior surface 104 of the body 102 of the bone-implantable device 100 will induce bone growth into the bone-implantable device 100 and be resorbed. The osteostimulative material 106 is eventually replaced by bone, thereby more firmly embedding the bone-implantable device 100 in the body.

The osteostimulative material 106 may take a variety of forms. The osteostimulative material 106 may allow for in-situ (i.e., in vivo) attachment of biological structures to each other and to manmade structures. The osteostimulative material 106 may also facilitate the repair of bone, ligaments, tendons and adjacent structures. The osteostimulative material 106 may also provide a bone substitute for surgical repair. The formulation of the osteostimulative material 106 is usable at numerous temperatures, pH ranges, humidity levels, and pressures. However, the formulation can be designed to be utilized at all physiological temperatures, pH ranges, and fluid concentrations. The osteostimulative material typically is, but not necessarily, injectable before curing and can exhibit neutral pH after setting. It may be absorbed by the host over a period of time.

The osteostimulative material 106 is particularly useful in situations (such as plastic surgery) when the use of metallic fasteners and other non-bioabsorbable materials are to be assiduously avoided. The osteostimulative material 106 also is useful when a certain amount of expansion or swelling is to be expected after surgery, e.g., in skull surgeries. It is a good platform for bone-formation. The osteostimulative material 106 can be also used as an anchoring device or grafting material.

Generally, the osteostimulative material 106 is derived from the hydrated mixture which comprises: (a) $KH_2PO_4$ in an amount between about 20-70 dry weight percent, (b) MgO in an amount between 10-50 dry weight percent, (c) a calcium containing compound, and (d) a sugar. In one particular example, the calcium containing compound is $Ca_5(PO_4)_3OH$.

Exemplary formulations of the osteostimulative material 106 include the following:

| Formulation I* | |
|---|---|
| Potassium phosphate (i.e., $KH_2PO_4$) | 61% |
| MgO (calcined) | 31% |
| $Ca_{10}(PO_4)_6(OH)_2$ | 4% |
| Sucrose $C_{12}H_{22}O_{11}$ (powder) | 4% |

*All values are weight percentages

Water is added up to about 40 weight percent of the dry formulation, preferably between about 20-35 weight percent, more preferably between 22-25 weight percent.

| Formulation II* | |
|---|---|
| $KH_2PO_4$ | 54% |
| MgO (calcined) | 33% |
| $Ca_{10}(PO_4)_6(OH)_2$ | 9% |
| Sucrose $C_{12}H_{22}O_{11}$ (powder) | 4% |

*All values are weight percentages

Water is added up to about 40 weight percent of the dry formulation, preferably between about 20-35 weight percent, more preferably between 22-25 weight percent.

| Formulation III* | |
|---|---|
| $KH_2PO_4$ | 44% |
| MgO (calcined) | 44% |
| Calcium-containing compound | 8% (whereby the compound is $Ca_{10}(PO_4)_6(OH)_2$ or $CaSiO_3$) |
| Sucrose $C_{12}H_{22}O_{11}$ (powder) | 4% |

*All values are weight percentages

Water is added up to about 40 weight percent of the dry formulation, preferably between about 20-35 weight percent, more preferably between 22-25 weight percent.

| Formulation IV* | |
|---|---|
| $KH_2PO_4$ | 44% |
| MgO (calcined) | 41% |
| $Ca_{10}(PO_4)_6(OH)_2$ | 8% |
| Sucrose $C_{12}H_{22}O_{11}$ (powder) | 4% |
| Mono-sodium phosphate (MSP) | 3% |

*All values are weight percentages

Water is added up to about 40 weight percent of the dry formulation, preferably between about 20-35 weight percent, more preferably between about 28-32 weight percent.

| Formulation V* | |
|---|---|
| Potassium phosphate (i.e., $KH_2PO_4$) | 41% |
| MgO (calcined) | 45% |
| Calcium-containing compound | 9% (whereby the compound is $Ca_{10}(PO_4)_6(OH)_2$, $CaSiO_3$ or combinations thereof.) |
| Sucrose $C_{12}H_{22}O_{11}$ (powder) | 1% |

*All values are weight percentages

Water is added up to about 40 weight percent of the dry formulation, preferably between about 20-35 weight percent, more preferably between 22-25 weight percent.

| Formulation VI* | |
|---|---|
| $KH_2PO_4$ | 45% |
| MgO (calcined) | 45% |
| $Ca_{10}(PO_4)_6(OH)_2$ | 8% |
| Sucralose | 2% |

*All values are weight percentages

Water is added up to about 40 weight percent of the dry formulation, preferably between about 20-35 weight percent, more preferably between 22-25 weight percent.

| Formulation VII* | |
|---|---|
| $KH_2PO_4$ | 61% |
| MgO (calcined) | 32% |
| $Ca_{10}(PO_4)_6(OH)_2$ | 4% |
| Dextrose | 1.5% |
| $\alpha$-$Ca_3(PO_4)_2$ | 1.5% |

*All values are weight percentages

Water is added up to about 40 weight percent of the dry formulation, preferably between about 20-35 weight percent, more preferably between 22-25 weight percent.

| Formulation VIII* | |
|---|---|
| $KH_2PO_4$ | 50% |
| MgO (calcined) | 35% |
| $Ca_{10}(PO_4)_6(OH)_2$ | 7% |
| $\beta\text{-}Ca_3(PO_4)_2$ | 3% |
| Dextrose | 5% |

*All values are weight percentages

Water is added up to about 40 weight percent of the dry formulation, preferably between about 20-35 weight percent, more preferably between 22-25 weight percent.

| Formulation IX* | |
|---|---|
| $KH_2PO_4$ | 54% |
| Phosphoric Acid | 4% |
| Metal oxide | 32% (wherein the metal oxide is MgO, ZrO, FeO or a combination thereof) |
| $Ca_{10}(PO_4)_6(OH)_2$ | 7% |
| Sucrose | 3% |

*All values are weight percentages

Water is added up to about 40 weight percent of the dry formulation, preferably between about 20-35 weight percent, more preferably between 22-25 weight percent.

| Formulation X* | |
|---|---|
| $KH_2PO_4$ | 61% |
| Metal oxide | 32% (wherein the metal oxide is MgO, Ca, FeO or a combination thereof) |
| $Ca_{10}(PO_4)_6(OH)_2$ | 6% |
| Sucrose | 1% |

*All values are weight percentages

Water is added up to about 40 weight percent of the dry formulation, preferably between about 20-35 weight percent, more preferably between 22-25 weight percent.

| Formulation XI* | |
|---|---|
| $KH_2PO_4$ | 45% |
| MgO (calcined) | 45% |
| $Ca_{10}(PO_4)_6(OH)_2$ | 10% |

*All values are weight percentages

Water is added up to about 40 weight percent of the dry formulation, preferably between about 20-35 weight percent, more preferably between 22-25 weight percent.

The above formulations and weight percents are merely exemplary. A range of dry constituents can also be used. For example, a suitable range for the phosphate (i.e., monopotassium phosphate (MKP)) is generally between about 20-70 weight percent, preferably between about 40-65 weight percent. In some situations and/or embodiments it is preferable to use the phosphate at a range between about 40-50 weight percent, while in others it may be preferable to use a range of about 50-65 weight percent.

A suitable range for the metal oxide (i.e., MgO) is generally between about 10-60, preferably between 10-50, and even more preferably between 30-50 weight percent. In some situations and/or embodiments it may be preferable to use between about 35 and 50 weight percent.

Calcium containing compounds can be added in various weight percentages. The calcium containing compound(s) is preferably added at about 1-15 weight percent, more preferably between about 1-10 weight percent. Higher percentages can be employed in certain situations.

Sugars (and/or other carbohydrate containing substances) are generally present at weight percent between 0.5 and 20, preferably about 0.5-10 weight percent of the dry composition.

Water (or another aqueous solution) can be added in a large range of weight percents generally ranging from about 15-40 weight percent, preferably between about 20-35 weight percent. For example, in certain embodiments of the materials as generally described herein, water or other aqueous solution is added at between about 28-32 weight percent. In other embodiments of the materials as generally described herein, water or other aqueous solution is added at between about 28-32 weight percent. It was found that a saline solution may be used. An exemplary saline solution is a 0.9% saline solution.

For some embodiments (i.e., formula III) it has been found that adding water at a weight percent of about 37 weight percent produces a creamy textured material that is extremely easy to work with, has excellent adhesive properties, and is easily injectable through a syringe.

The noted ranges may vary with the addition of various fillers and other components or for other reasons.

In one embodiment, the weight percent ratio between MKP and MgO is between about 4:1 and 0.5:1. In another it is between approximately 2:1 and 1:1.

Without limiting the invention in any manner, in such an embodiment the inventors surmise that the un-reacted magnesium is at least partly responsible for the in vivo expandability characteristics of the bio-adhesive. Specifically the metal oxide (i.e., magnesium oxide) reacts with water and serum in and around the living tissue to yield $Mg(OH)_2$ and magnesium salts. It has been found that in some embodiments the material generally expands to between 0.15 and 0.20 percent of volume during curing in moisture. The expansion of the material is believed to increase the adhesive characteristics of the material. For example, the disclosed material has been shown to effectively attach soft tissues like ligaments to bone, the expansion of the material improving adhesion through mechanical strength.

Osteostimulative material 106 useful in the present invention can also be found in U.S. Pat. Nos. 6,533,821, 6,787,495, 7,045,476, 9,078,884, U.S. Patent Application Publication No. 2015/0250924, and U.S. Patent Application Publication No. 2015/0314045, all of which are hereby incorporated by reference in their entirety.

In operation, the present invention provides a method for securing a bone portion using a bone-implantable device, the method comprising: (a) providing the bone-implantable device, the bone-implantable device comprising a body having an exterior surface with a portion of the exterior surface comprising a cured, MgO-containing osteostimulative material, and (b) securing the bone-implantable device to the bone portion so that said cured osteostimulative material contacts the bone portion.

In one embodiment, providing the bone-implantable device includes applying an uncured osteostimulative material to the exterior surface of the bone-implantable device and curing the uncured osteostimulative material before securing the bone-implantable device to the bone portion.

As discussed above, a thickness of the cured osteostimulative material on the exterior surface of the body may range from about 20 μm to about 200 μm. In such an embodiment, applying the uncured osteostimulative material to the exterior surface of the bone-implantable device may comprise one or more of spraying the uncured osteostimulative material on the exterior surface of the bone-implantable device, dipping the bone-implantable device in the uncured osteostimulative material, and brushing the osteostimulative material onto the exterior surface of the bone-implantable device.

Further, curing the uncured osteostimulative material may comprise heat treating the bone-implantable device after the uncured osteostimulative material is applied to the exterior surface of the bone-implantable device. Because high deposition temperature is needed in order to obtain high quality of MgO films, the curing temperature may be varied from 400° C. to 500° C. in 25° C. intervals. The annealing curing is inversely proportional to the thickness of the mixture of osteostimulative material. After cooking in an oven, the bone-implantable device may then be air dried. The process of heat treating will reduce drying time exponentially compared with just applying the osteostimulative material to the exterior surface of the bone-implantable device and allowing it to cure without the aid of heat.

In another embodiment, the body of the bone-implantable device further comprises an internal cavity and one or more openings connecting the interior cavity to the exterior surface. In such an embodiment, the method may further include applying an uncured osteostimulative material to the interior cavity and the one or more openings of the bone-implantable device and curing the uncured osteostimulative material before securing the bone-implantable device to the bone portion.

In yet another embodiment, the method further includes applying an uncured osteostimulative material to the exterior surface of the bone-implantable device, curing the uncured osteostimulative material as discussed above, and packaging the bone-implantable device in a container for future use. As such, the bone-implantable device would include the cured osteostimulative material at the point of sale. Current procedures require a medical professional to add bone cement either just before the implant is inserted into the body or after the implant has already been inserted into the body. As such, providing a bone-implantable device with a cured osteostimulative material at the point of sale is an improvement that expedites the procedure for a medical professional.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Because many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A bone-implantable device comprising:
   a body having an exterior surface, wherein a portion of the exterior surface includes a cured osteostimulative material comprising $KH_2PO_4$ in an amount between 20-70 dry weight percent, MgO in an amount between 10-50 dry weight percent, a calcium containing compound, and a sugar.

2. The bone-implantable device of claim 1, wherein the exterior surface includes a plurality of grooves, and wherein the cured osteostimulative material is positioned in one or more of the plurality of grooves.

3. The bone-implantable device of claim 1, wherein the body includes an interior cavity and one or more openings connecting the interior cavity to the exterior surface, and wherein at least a portion of the interior cavity and at least a portion of the one or more openings includes the cured osteostimulative material.

4. The bone-implantable device of claim 1, wherein the bone-implantable device comprises a bone screw including a head portion and a threaded portion, and wherein at least a portion of the threaded portion includes the cured osteostimulative material.

5. The bone-implantable device of claim 1, wherein the bone-implantable device comprises an inter-vertebrate implant having a top grooved surface and a bottom grooved surface, wherein at least a portion of each of the top grooved surface and the bottom grooved surface includes the cured osteostimulative material.

6. The bone-implantable device of claim 1, wherein the body comprises titanium, polyetheretherketone (PEEK), polyurethane, or bone.

7. The bone-implantable device of claim 1, wherein the calcium containing compound is $Ca_5(PO_4)_3OH$.

8. The bone-implantable device of claim 1, wherein the exterior surface includes a plurality of pores, and wherein the cured osteostimulative material is positioned in one or more of the plurality of pores.

9. The bone-implantable device of claim 1, wherein the cured osteostimulative material has osteoconductive and osteoinductive properties.

10. The bone-implantable device of claim 1, wherein the cured osteostimulative material is bioresorbable.

11. The bone-implantable device of claim 1, wherein a thickness of the cured osteostimulative material on the exterior surface of the body ranges from 20 μm to 200 μm.

12. A method for securing a bone portion using the bone-implantable device of claim 1, the method comprising:
    providing the bone-implantable device of claim 1; and
    securing the bone-implantable device to the bone portion so that said cured osteostimulative material contacts the bone portion.

13. The method of claim 12, further comprising:
    applying the uncured osteostimulative material to the exterior surface of the bone-implantable device; and
    curing the uncured osteostimulative material before securing the bone-implantable device to the bone portion.

14. The method of claim 13, wherein applying the uncured osteostimulative material to the exterior surface of the bone-implantable device comprises one or more of spraying the uncured osteostimulative material on the exterior surface of the bone-implantable device, dipping the bone-implantable device in the uncured osteostimulative material, and brushing the osteostimulative material onto the exterior surface of the bone-implantable device.

15. The method of claim 13, wherein curing the uncured osteostimulative material comprises heat treating the bone-implantable device.

16. The method of claim 13, wherein the body of the bone-implantable device further comprises an internal cavity and one or more openings connecting the interior cavity to the exterior surface, the method further comprising:
    applying the uncured osteostimulative material to the interior cavity and the one or more openings of the bone-implantable device; and curing the uncured osteostimulative material before securing the bone-implantable device to the bone portion.

17. The method of claim 12, further comprising:
applying the uncured osteostimulative material to the exterior surface of the bone-implantable device;
curing the uncured osteostimulative material; and
packaging the bone-implantable device in a container for future use.

\* \* \* \* \*

UNITED STATES PATENT AND TRADEMARK OFFICE
CERTIFICATE OF CORRECTION

| | | |
|---|---|---|
| PATENT NO. | : 10,722,280 B2 | Page 1 of 1 |
| APPLICATION NO. | : 15/939981 | |
| DATED | : July 28, 2020 | |
| INVENTOR(S) | : Frankie L. Morris et al. | |

It is certified that error appears in the above-identified patent and that said Letters Patent is hereby corrected as shown below:

On the Title Page

Item (72) Inventors:
Replace: "Frankie L. Morris, Colleyville, TX (US); Drew Diaz, Colleyville, TX (US)"

With --Frankie L. Morris, Colleyville, TX (US); Drew Diaz, Colleyville, TX (US); Brandon Roller, Colleyville, TX (US)--

Signed and Sealed this
Eighteenth Day of July, 2023

Katherine Kelly Vidal
*Director of the United States Patent and Trademark Office*